United States Patent [19]

Hall et al.

[11] 4,242,342

[45] Dec. 30, 1980

[54] QUINOXALINONES USEFUL FOR TREATING ATOPIC ECZEMA AND URTICARIA

[75] Inventors: Charles M. Hall; Herbert G. Johnson, both of Kalamazoo, Mich.

[73] Assignee: The Upjohn Company, Kalamazoo, Mich.

[21] Appl. No.: 44,031

[22] Filed: May 31, 1979

Related U.S. Application Data

[62] Division of Ser. No. 940,815, Sep. 11, 1978, Pat. No. 4,181,724.

[51] Int. Cl.³ ........................................... A61K 31/495
[52] U.S. Cl. ...................................................... 424/250
[58] Field of Search ........................................ 424/250

[56] References Cited

U.S. PATENT DOCUMENTS

| | | | |
|---|---|---|---|
| 3,582,315 | 6/1971 | Soper | 71/92 |
| 3,770,727 | 11/1973 | Brack | 544/105 |
| 4,075,206 | 2/1978 | Holmes | 544/344 |

*Primary Examiner*—Leonard Schenkman
*Attorney, Agent, or Firm*—Martin B. Barancik

[57] ABSTRACT

Compounds of the formula below are useful for expanding the lumina of air passages in a mammal in need of said treatment. The compounds are also useful for treating atopic eczema and urticaria.

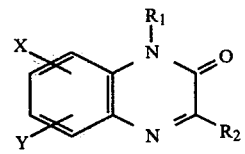

wherein X and Y are the same or different and are hydrogen, fluoro, chloro, bromo, nitro, trifluoromethyl, alkyl of one to four carbon atoms, inclusive, alkoxy of one to four carbon atoms, inclusive, and cyano;

$R_1$ is hydrogen, methyl or ethyl;

$R_2$ is hydrogen, alkyl of one to six carbon atoms, inclusive, phenyl, benzyl, $CH_2Z$ wherein Z is fluoro, chloro, or bromo, $CO_2M$, $CH_2CO_2M$, $CH_2CH_2CO_2M$ and $CHR_3CO_2M$ wherein M is hydrogen, alkyl of one to four carbon atoms, inclusive, or a physiologically acceptable metal or amine cation and $R_3$ is alkyl of one to three carbon atoms, inclusive, with the proviso that M is not hydrogen when $R_2$ is $CH_2CO_2M$ or $CHR_3CO_2M$.

1 Claim, No Drawings

QUINOXALINONES USEFUL FOR TREATING ATOPIC ECZEMA AND URTICARIA

This is a division of application Ser. No. 940,815, filed Sept. 11, 1978, now U.S. Pat. No. 4,181,724.

BRIEF SUMMARY OF THE INVENTION

It has been discovered that compounds of FIG. 1 are useful for expanding the lumina or air passages in the lungs in a mammal in need of said treatment. The compounds are formulated with pharmaceutical carriers for oral, parenteral, or inhalation means of administration. Certain compounds of the genus are novel.

DETAILED DESCRIPTION OF THE INVENTION

In accordance with this invention there is provided a method for expanding the lumina or air passages in the lungs in a mammal in need of said treatment which comprises administering an effective amount of a compound of the formula

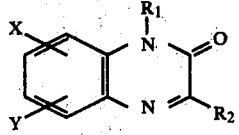

FIG. I wherein
X and Y are the same or different and are hydrogen, fluoro, chloro, bromo, nitro, trifluoromethyl, alkyl of one to four carbon atoms, inclusive, alkoxy of one to four carbon atoms, inclusive, and cyano;
$R_1$ is hydrogen, methyl or ethyl;
$R_2$ is hydrogen, alkyl of one to six carbon atoms, inclusive, phenyl, benzyl,
$CH_2Z$ wherein Z is fluoro, chloro, or bromo,
$CO_2M$, $CH_2CO_2M$, $CH_2CH_2CO_2M$ and $CHR_3CO_2M$ wherein M is hydrogen, alkyl of one to four carbon atoms, inclusive, or a physiologically acceptable metal or amine cation and $R_3$ is alkyl of one to three carbon atoms, inclusive, with the proviso that M is not hydrogen when $R_2$ is $CH_2CO_2M$ or $CHR_3CO_2M$ in association with a pharmaceutical carrier.

It should be noted that when $R_1$ of the compounds of FIG. I is hydrogen, the compounds of that figure can exist in varying quantities as the tautomeric structure and are considered part of the invention.

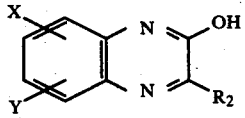

FIG. Ia

A further method of treatment is with compounds of FIG. I wherein
X and Y are the same or different and are hydrogen, fluoro, chloro, bromo, nitro, trifluoromethyl, alkyl of one to three carbon atoms, alkoxy of one to three carbon atoms, inclusive, and cyano;
$R_1$ is hydrogen, methyl or ethyl;
$R_2$ is hydrogen, alkyl of one to three carbon atoms, inclusive, phenyl, benzyl,
$CH_2Z$ wherein Z is fluoro, chloro, or bromo,
$CO_2M$, $CH_2CO_2M$, $CH_2CH_2CO_2M$ and $CHR_3CO_2M$ wherein $R_3$ and M are as defined above with the additional proviso that M is not a physiologically acceptable amine cation.

Another method of treatment is with compounds of FIG. I wherein X and Y are the same or different and are hydrogen, chloro, bromo, trifluoromethyl, alkyl of one to three carbon atoms, inclusive, alkoxy of one to three carbon atoms, inclusive, and cyano; $R_1$ is hydrogen, methyl or ethyl; $R_2$ is hydrogen, alkyl of one to three carbon atoms, inclusive, phenyl or benzyl.

A further method of treatment is with compounds of FIG. I of the various above groups wherein X is hydrogen.

Another method of treatment is with compounds of FIG. I of the various above groups wherein $R_1$ is methyl.

A still further method of treatment is with compounds of FIG. I of the various above groups wherein X is hydrogen and $R_1$ is methyl.

Among the novel compounds of this invention are:

| Compound | Melting Point |
| --- | --- |
| 1,3,6,7-tetramethyl-2-(1H)-quinoxalinone | 165.5–166.5° C. |
| 1-ethyl-3-methyl-2-(1H)-quinoxalinone | 94–95.5° C. |
| Methyl 3,4-dihydro-4-methyl-3-oxo-2-quinoxalinepropionate | 112–113° C. |
| 3-methyl-8-nitro-2-(1H)-quinoxalin-2-one | 247–248° C. |
| 3-methyl-5-nitro-2-(1H)-quinoxalin-2-one | 229–230° C. |
| 1,3-dimethyl-5-nitro-2-(1H)-quinoxalinone | 197–198° C. |
| 6,7-dichloro-1,3-dimethyl-2-(1H)-quinoxalinone | 224.5–226.5° C. |

As employed in this specification and throughout the claims, the phrase "alkyl of one to six carbon atoms, inclusive" means methyl, ethyl, propyl, pentyl, hexyl, and isomers thereof. Illustrative examples of isomers are isopropyl, t-butyl, neopentyl, and 2,2-dimethylbutyl. Alkyl of a smaller number of carbon atoms has a similar scoping.

The phrase "physiologically acceptable amine salt" refers to amines which are accepted by mammals in an essentially non-toxic manner when administered to mammals in conjunction with the acid moiety of the invention. Illustrative of the amines are those derived from primary, secondary or tertiary amines. Examples of suitable amines are methylamine, dimethylamine, triethylamine, ethylamine, dibutylamine, triisopropylamine, N-methyl-hexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, adamantylamines, and like aliphatic, cycloaliphatic, and araliphatic amines containing up to and including about eighteen carbon atoms as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-1-ethyl-1,3-propanediol, 2-amino-2-methyl-1-propanol, tris(hydroxymethyl)aminomethane, N-phenylethanolamine, N-(p-tert-amylphenyl)diethanolamine, galactamine, N-methylglucamine, N-methylglucosamine, ephedrine, phenylephrine, epinephrine, procaine, and the like. Also included within the amine scope are quaternary amines such as ammonium, tetramethylammonium, tetraethylammonium, benzyltrimethylammonium, phenyltriethylammonium, and the like.

The term "physiologically acceptable metal" includes alkali metals such as sodium and potassium, alkaline earth metals such as calcium and magnesium, and other acceptable metals such as aluminum.

The compounds used in the method of this invention can be prepared by general processes known to the art. Many of the compounds per se are already known in the art. A preferred route of synthesis is reacting X and Y substituted o-phenylene diamine with an α-keto ester or acid of the formula

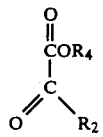

FIG. II wherein $R_2$ is the same $R_2$ group as defined in FIG. I and $R_4$ is hydrogen or alkyl of one to three carbon atoms, inclusive, to make compounds of FIG. I wherein $R_1$ is hydrogen. Compounds of FIG. I wherein $R_1$ is methyl or ethyl are then prepared by alkylation of the compounds of FIG. I wherein $R_1$ is hydrogen.

The reaction of the α-keto ester or acid with the o-phenylene diamine is accomplished neat using excess α-keto compound or a solvent such as tetrahydrofuran, dioxane, diethylether, methylene chloride, chloroform, acetone, dimethylformamide and the like can be employed.

The N-alkylation reaction is carried out in a polar, inert solvent such as dimethylformamide, dimethylacetamide, anhydrous diglymine and the like in the presence of a base such as sodium carbonate and the like. The temperature of the alkylation reaction is generally slightly elevated over room temperature. Temperature of about 35° to about 80° C. for a period of about two to about twenty-four hours will bring about reasonable yields of N-alkylated compound.

An alternative route for making compounds of the invention wherein $R_2$ is $CH_2CO_2M$ and $CHR_3CO_2M$ starts by reacting an appropriately X and Y substituted ortho phenylene diamine with a dicarboxylate of the formula

FIG. III wherein $R_4$ is as defined above to produce compounds of the formula

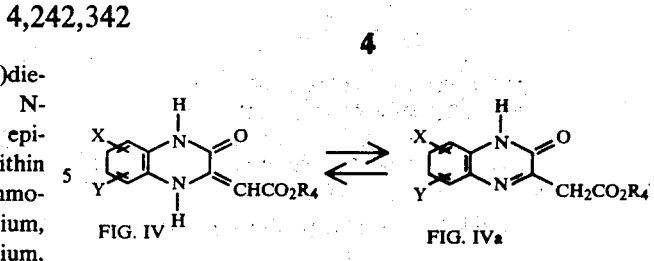

the compounds of FIGS. IV and IVa being tautomers. This reaction can be carried out in alcohols or non-protic solvents having one to four carbon atoms at room temperature for extended periods of time, that is, six to eighteen hours.

The compounds of FIGS. IV and IVa can be converted to alkylated quinoxalinones by reaction of the compounds of FIGS. IV or IVa with sodium carbonate or a base of equivalent strength with a molar excess of $R_1I$ in dimethylformamide or equivalent solvent at room temperature for four to eight hours.

The alkylated quinoxalinone prepared immediately above can be converted to a compound wherein $R_2$ is $CHR_3CO_2R_4$ by reaction with excess $R_3I$ in sodium carbonate or a base of equivalent strength in a solvent such as dimethylformamide, dimethylacetamide or diglyme at a temperature of 70°-100° C. for a period of about twelve to twenty-four hours.

To prepare compounds of FIG. I wherein $R_2$ is $CHR_3CO_2M$ and $R_1$ is hydrogen, the compound of FIG. IV is reacted in a solvent such as anhydrous tetrahydrofuran, dimethylether, dioxane, and diglyme with two equivalents of a strong base such as an alkyl lithium or sodium hydride and an equivalent of alkylating agent such as $R_3I$. The reaction is maintained for about two to four hours at room temperature and the desired compound is recovered.

It should be noted that compounds wherein $R_4$ is present can be readily converted to salts of the acid through standard synthetic methods such as treatment with strong base.

Following are illustrative examples of starting materials which can be used to prepare compounds utilized in this invention.

TABLE I

| X | Y |
|---|---|
| 4-Br | H |
| 4-OC$_4$H$_9$ | H |
| 4-C$_4$H$_9$ | H |
| 4-CF$_3$ | H |
| 4t-C$_4$H$_9$ | H |
| 4-CN | H |
| 3-Cl | H |
| 4-i-C$_4$H$_9$ | H |
| 4-Cl | H |
| 4-C$_2$H$_5$ | H |
| 4-OC$_2$H$_5$ | H |
| 3-F | H |
| 4-F | H |
| 4i-C$_3$H$_7$ | H |
| 4-OCH$_3$ | H |
| 3-OCH$_3$ | H |
| 3-CH$_9$ | H |
| 3-Cl | 5-Br |
| 3-tC$_4$H$_9$ | 6-tC$_4$H$_9$ |
| 3-Cl | 4-Cl |
| 4-Cl | 5-Cl |
| 4-OCH$_3$ | 5-OCH$_3$ |

TABLE I-continued

| | |
|---|---|
| 4-CH$_3$ | 5-CH$_3$ |
| 4-NO$_2$ | 5-NO$_2$ |
| 4-Cl | 5-Br |
| 3-CN | 5-CF$_3$ |
| 3-OC$_2$H$_5$ | 6-NO$_2$ |
| 4-CF$_3$ | 5-CF$_3$ |
| 3-Br | 6-C$_4$H$_9$ |
| 3-OiC$_4$H$_9$ | 5-Cl |
| 4-CN | 6-OC$_2$H$_5$ |
| 3-CF$_3$ | 5 CN |
| 4-NO$_2$ | 5-CH$_3$ |

$$\begin{array}{c} O \\ \parallel \\ COR_4 \\ | \\ C \\ \diagup \diagdown \\ O \quad R_2 \end{array}$$

| R$_2$ | R$_4$ |
|---|---|
| H | H |
| CH$_3$ | C$_2$H$_5$ |
| BrCH$_2$ | H |
| FCH$_2$ | H |
| C$_2$H$_5$O$_2$C | C$_2$H$_5$ |
| C$_6$H$_5$ | H |
| C$_5$H$_5$CH$_2$ | H |
| CH$_3$CH$_2$ | H |
| HO$_2$CCH$_2$CH$_2$ | H |

| | |
|---|---|
| CO$_2$R$_4$ | |
| \| | |
| C | |
| ||| | |
| C | |
| \| | |
| CO$_2$R$_4$ | |
| R$_4$ | |
| CH$_3$ | |
| i-C$_3$H$_7$ | |
| C$_2$H$_5$ | |
| C$_3$H$_7$ | | the following are examples of compounds which can be used in accordance with this invention. All temperatures are centigrade.

EXAMPLE 1

3,6,7-Trimethyl-2(1H)-quinoxalinone 4,5-Dimethyl-o-phenylenediamine (10.0 g., 0.073 mol.) was dissolved in tetrahydrofuran (200 ml.) and ethyl pyruvate (12.75 g., 0.11 mol.) added. The reaction mixture was stirred at room temperature for eighteen hours, during which time a white solid precipitated and was collected by filtration (13.35 g.) Recrystallization from methanol-chloroform gave fine white needles. (12.65 g., m.p. 306°–308°, 92%).

Analysis Calc'd for: C$_{11}$H$_{12}$ON$_2$. C, 70.19; H, 6.43; N, 14.89. Found: C, 70.17; H, 6.40; N, 14.99.

EXAMPLE 2

3-(Bromomethyl)-2(1H)-Quinoxalinone

O-phenylenediamine (1.0 g., 0.0092 mol.) was dissolved in tetrahydrofuran (50 ml.) and 3-bromopyruvic acid (1.7 g., 0.0102 mol.) added. The reaction mixture was stirred at room temperature for one hour, during which time the product precipitated as a yellow solid. The product was collected by filtration and crystallized from methylene chloride. (0.91 g., m.p. 221°–223° (dec.) 41%)

Analysis Calc'd for: C$_9$H$_7$ON$_2$Br. C, 45.21; H, 2.95; N, 11.72; Br, 33.43. Found: C, 45.38; H, 2.82; N, 12.04; Br, 33.57.

EXAMPLE 3

1-Methyl-3-bromomethyl-2(1H)-quinoxalinone

N-bromosuccinimide (3.36 g., 0.0189 mol.) and benzoyl peroxide (0.06 g.) were added to a solution of 1,3-dimethyl-2(1H)-quinoxalinone (3.0 g., 0.017 mol.) in carbon tetrachloride (250 ml.). The mixture was heated at reflux for four hours. Removal of the solvent left a tan solid. Chromatography on silica gel with methylene-chloride as the eluent gave a tan solid. Recrystallization from methylene-chloride gave light tan needles. (2.33 g., m.p. 192.5°–193.5°, 53%).

Analysis Calc'd for: C$_{10}$H$_3$ON$_2$Br. C, 47.45; H, 3.58; N, 11.07; Br, 31.53. Found: C, 47.56; 3.71; N, 10.96; Br, 31.83.

EXAMPLE 4

1,3,6,7-Tetramethyl-2(1H)-quinoxalinone

A mixture of 3,6,7-trimethyl-2(1H)-quinoxalinone (5.0 g., 0.027 mol.), methyl iodide (15 ml.), sodium carbonate (5.0 g., 0.047 mol.) and dimethylformamide (75 ml.) were stirred at room temperature for eighteen hours, then heated at 75°–80° C. for three hours. Removal of the dimethylformamide under reduced pressure and dilution with water gave a brown solid. Crystallization from acetone (Darco) gave light tan needles. (2.85 g., m.p. 164°–166°, 53%).

Analysis Calc'd for: C$_{12}$H$_{14}$ON$_2$. C, 71.26; H, 6.98; N, 13.85. Found: C, 71.31; H, 7.03; N, 13.73.

EXAMPLE 5

Methyl 3,4-dihydro-3-oxo-2-quinoxalineacetate

Dimethyl acetylenedicarboxylate (31.2 g., 0.22 mol.) was added slowly to a solution of o-phenylenediamine (21.6 g., 0.2 mol.) in methanol (400 ml.). The reaction mixture was stirred at room temperature for three hours and then cooled in an ice bath. The yellow solid was collected and washed with cold methanol. The solid was recrystallized from tetrahydrofuran (27.7 g., m.p. 230°–232° dec.).

EXAMPLE 6a

Methyl 3,4-Dihydro-α-methyl-3-oxo-2-quinoline-acetate

To a mixture of methyl 3,4-dihydro-3-oxo-2-quinoxaline-acetate (5.0 g., 0.023 mol.) in tetrahydrofuran (250 ml.), butyl lithium (1.6 m, 29 ml., 0.046 mol.) was added slowly. The reaction mixture became clear and then a yellow precipitate formed. Methyl iodide (3.26 g., 0.023 mol.) was added slowly to give a clear solution. The reaction mixture was stirred at room temperature for two hours. About 200 ml. of solvent was removed under reduced pressure and the residue was poured into 1 N hydrochloric acid (93 ml.). A brown precipitate formed and was collected by filtration (3.7 g.). Recrystallization from acetone-Skellysolve B twice gave the desired material (182°–183°, 1.8 g., 34%).

Analysis Calc'd for: C$_{12}$H$_{12}$N$_2$O$_3$. C, 62.06; H, 5.21; N, 12.07. Found: C, 61.88; H, 5.05; N, 12.16.

EXAMPLE 6b 3,4-Dihydro-α,4-dimethyl-3-oxo-2-quinoxaline-acetate

A mixture of methyl 3,4-dihydro-3-oxo-2-quinoline-acetate (4.0 g., 0.018 mol.), anhydrous dimethylformamide (50 ml.) anhydrous sodium carbonate and methyl iodide (20 ml.) were heated in an oil bath (100°) for eighteen hours. The sodium carbonate was removed by filtration from the cooled reaction mixture. The excess dimethylformamide was removed under reduced pressure. Water was added to the residue to give a solid. The solid was recrystallized from Skellysolve B to give a yellow solid (1.94 g., m.p. 77°-78°).

Analysis Calc'd for: $C_{13}H_{14}N_2O_3$. C, 63.40; H, 5.73; N, 11.38. Found: C, 63.32; H, 5.71; N, 11.40.

EXAMPLE 7

Following the procedure of the above examples, the following compounds are made.

| X | Y | $R_1$ | $R_4$ | M.P. °C. |
|---|---|---|---|---|
| H | H | $C_2H_5$ | $CH_3$ | 94-95.5 |
| 6-Cl | 7-Cl | H | $CH_3$ | >320° |
| 6-Cl | 7-Cl | $CH_3$ | $CH_3$ | 224.5-226.5° |
| H | H | H | H | 272° |
| H | H | $CH_3$ | $CH_2CH_2CO_2CH_3$ | 112-113° |
| H | H | H | $CH_2CH_2CO_2H$ | 285° |
| H | H | $CH_3$ | $C_2H_5$ | 104-105° |
| H | H | H | $C_2H_5$ | 202-203° |
| H | H | $CH_3$ | $CO_2H$ | 180-182° |
| H | H | $CH_3$ | $CO_2C_2H_5$ | 121-122° |
| H | H | H | $CO_2C_2H_5$ | 165° |
| H | H | H | $CO_2H$ | 223-225° |
| H | H | $CH_3$ | Ph | 135-137° |
| H | H | H | Ph | 248-250° |
| H | 5-$NO_2$ | H | $CH_3$ | 255° |
| H | 8-$NO_2$ | H | $CH_3$ | 231-233° |
| H | H | $CH_3$ | H | 120-121° |
| H | H | $CH_3$ | $CH_3$ | 85-87° |
| H | H | H | $CH_3$ | 250-251° |
| H | H | $CH_3$ | $CH_2CH_2CO_2H$ | 180-182° |
| H | 5-$NO_2$ | $CH_3$ | $CH_3$ | 197-198° |
| H | 8-$NO_2$ | $CH_3$ | $CH_3$ | 120-122° |
| H | 5-$NO_2$ | H | H | 247-248° |
| H | 8-$NO_2$ | H | H | 229-230° |

The compounds of this invention are useful for treating conditions wherein bronchodilation is important. Examples of such conditions are bronchial asthma, exercise-induced asthma, and similar conditions. In treating the conditions standard pharmaceutical compositions are employed. The compositions of the present invention are presented for administration to humans and animals in unit dosage forms such as tablets, capsules, pills, powders, granules, sterile parenteral solutions or suspensions, oral solutions or suspensions, and wherein the specific compound is sufficiently soluble in the target tissue, the compound is delivered by aerosol or insufflation technique.

For oral administration, either solid or fluid unit dosage forms can be prepared. For preparing solid compositions such as tablets, the compound of Formula I is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the compositions to facilitate uniform distribution of the compound.

The preferred compositions are those for oral administration.

Compositions for inhalation are of three basic types: (1) a powder mixture preferably micropulverized with particle size, preferably from about one to about five microns; (2) an aqueous solution to be sprayed with a nebulizer; and (3) an aerosol with volatile propellant in a pressurized container.

The powders are quite simply prepared by mixing a compound of FIG. I with a solid base which is compatible with lung tissue, preferably lactose. The powders are packaged in a device adapted to emit a measured amount of powder when inhaled through the mouth.

Aqueous solutions are prepared by dissolving the compound of FIG. I in water and adding salt to provide an isotonic solution and buffering to a pH compatible with inhalation. The solutions are dispersed in a spray device or nebulizer and sprayed into the mouth while inhaling.

Aerosols are prepared by dissolving a compound of FIG. I in water or ethanol and mixing with a volatile propellant and placing in a pressurized container having a metering valve to release a predetermined amount of material.

The liquefied propellant employed is one which has a boiling point below 65° F. at atmospheric pressure. For use in compositions intended to produce aerosols for medicinal use, the liquefied propellant should be nontoxic. Among the suitable liquefied propellants which may be employed are the lower alkanes containing up to five carbon atoms, such as butane and pentane or a lower alkyl chloride, such as ethyl, or propyl chlorides.

Further suitable liquefied propellants are the fluorinated and fluorochlorinated lower alkanes such as are sold under the trademark "Freon" and "Genetron". Mixtures of the above-mentioned propellants may suitably be employed. Examples of these propellants are dichlorodifluoromethane ("Freon 12"), dichlorotetrafluoroethane ("Freon 114"), trichloromonofluoromethane ("Freon 11"), dichloromonofluoromethane ("Freon 21"), monochlorodifluoromethane ("Freon 22"), trichlorotrifluoroethane ("Freon 113"), difluoroethane ("Genetron 142-A") and monochlorotrifluoromethane ("Freon 13").

The term "unit dosage form", as used in the specification and claims, refers to physically discrete units suitable as unitary dosages for human subjects and animals, each unit containing a predetermined quantity of active material calculated to produce the desired therapeutic effect. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, wafers, granules, cachets, teaspoonfuls, tablespoonfuls, dropperfuls, ampuls, vials, aerosols with metered discharges, segregated multiples of any of the foregoing, and other forms as herein described.

An effective but non-toxic quantity of the compound is employed in treatment. The dosage of the compound for treatment depends on the route of administration and the potency of the particular compound. A dosage schedule for humans of from about 0.1 to about 200 mg. of compound in a single dose administered parenterally or by inhalation in the compositions of this invention is effective for four to six hours. More specifically, the dose is from about 1 to about 40 mg. of compound. The oral dose is from about 0.1 to about 200 mg. in a single dose. More specifically, the single dose is from about 5 to about 50 mg. of compound. The dosage to be administered can be repeated up to four times daily.

The administration of the compounds of the present invention to humans and animals provides a method for expanding the lumina or air passages of the lungs. Such activity is useful in treating bronchial asthma, and "intrinsic asthma".

EXAMPLE 8

A lot of 10,000 tablets is prepared from the following types and amounts of ingredients:

| | |
|---|---|
| 1,3-dimethyl-2(1H)-quinoxalinone | 250 gm. |
| Dicalcium phosphate | 1,000 gm. |
| Methylcellulose, U.S.P. (15 cps) | 60 gm. |
| Talc | 150 gm. |
| Corn starch | 200 gm. |
| Magnesium stearate | 10 gm. |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets.

These tablets are useful in treating asthma at a dose of one table every four to six hours.

EXAMPLE 9

One thousand two-piece hard gelatin capsules are prepared from the following types and amounts of ingredients:

| | |
|---|---|
| 1,3-dimethyl-2(1H)-quinoxalinone | 25 gm. |
| Talc | 50 gm. |
| Lactose | 100 gm. |
| Magnesium stearate | 1 gm. |

The ingredients are mixed well and filled into capsules of the proper size.

Capsules so prepared are useful in treating asthma at a dose of one capsule every four to six hours.

EXAMPLE 10

A sterile preparation suitable for intramuscular injection is prepared from the following ingredients:

| | |
|---|---|
| 1,3-dimethyl-2(1H)-quinoxalinone | 50 gm. |
| Benzyl benzoate | 200 ml. |
| Methylparaben | 1.5 gm. |
| Propylparaben | 0.5 gm. |
| Cottonseed oil q.s. | 1,000 ml. |

One milliliter of this sterile preparation is injected for treatment of asthma.

EXAMPLE 11

Six hundred ml. of an aqueous solution is prepared as follows:

| | |
|---|---|
| 1,3-dimethyl-2(1H)-quinoxalinone | 1 gm. |
| Sodium chloride | 5 gm. |
| Water for injection q.s. | 600 ml. |

The compound and sodium chloride are dissolved in sufficient water to make 600 ml. and sterile filtered.

The solution is placed in nebulizers designed to deliver 0.25 ml. of solution per spray.

The solution is inhaled into the lungs every four to six hours for treatment of bronchial asthma attacks.

EXAMPLE 12

A powder mixture consisting of 2 grams of 1,3-dimethyl-2(1H)-quinoxalinone and sufficient lactose to make five grams of mixture is micropulverized and placed in an insufflator designed to deliver 50 mg. of powder per dose.

The powder is inhaled into the lungs every four to six hours of prevention of asthmatic attacks.

EXAMPLE 13

Twelve grams of an aerosol composition are prepared from the following ingredients:

| | |
|---|---|
| 1,3-dimethyl-2(1H)-quinoxalinone | 0.50 gm. |
| Freon 12 | 1.44 gm. |
| Freon 114 | 2.16 gm. |
| Water | 7.30 gm. |
| Sorbitan monooleate | 0.60 gm. |

The compound is dissolved in the water and added to the Freons. The twelve grams of compositions are added to a 13 cc. plastic coated bottle and capped with a metering valve. The metering valve releases 80 mg. of composition in an aerosol. The aerosol is inhaled every four to six hours for treatment of intrinsic asthma.

EXAMPLE 14

After allowing the inter alia for the different solubilities of the compounds and the activity of the particular compounds as measured, for example, by the rat passive cutaneous anaphylaxis assay (PCA) and the phosphodiesterase inhibition assay, a suitable quantity of each of the compounds of Table I and Examples 1–7 is substituted in the compositions of Examples 8–13 and results showing activity are obtained.

The preferred compound is 1,3-dimethyl-2-(1H)-quinoxalinone.

The compounds of the invention have adenyl cyclase activity as well and can be used to treat atopic eczema and urticaria as well by using the same systemic modes of delivery within the same dosage ranges as disclosed above.

Although the claim formulae are limited to only one of the tautomeric structures, it is intended that all the tautomeric forms be included within the claim language.

We claim:

1. A method for treating atopic eczema or urticaria in a mammal in need of said treatment which comprises administering to said mammal an effective amount of a compound of the formula

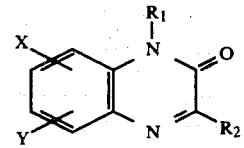

wherein
X and Y are the same or different and are hydrogen, fluoro, chloro, bromo, nitro, trifluoromethyl, alkyl of one to four carbon atoms, inclusive, alkoxy of one to four carbon atoms, inclusive, or cyano;
$R_1$ is hydrogen, methyl or ethyl,
$R_2$ is hydrogen, alkyl of one to six carbon atoms, inclusive, phenyl, benzyl,
$CH_2Z$ wherein Z is fluoro, chloro or bromo,
$CO_2M$, $CH_2CO_2M$, $CH_2CH_2CO_2M$ or $CHR_3CO_2M$ wherein M is hydrogen, alkyl of one to four carbon atoms, inclusive, or a physiologically acceptable metal or amine cation and $R_3$ is alkyl of one to three carbon atoms, inclusive, with the proviso that M is not hydrogen when $R_2$ is $CH_2CO_2M$ or $CHR_3CO_2M$; in association with a pharmaceutical carrier.

* * * * *